United States Patent [19]

Mihara

[11] Patent Number: 5,958,928
[45] Date of Patent: Sep. 28, 1999

[54] PHARMACEUTICAL AGENTS CONTAINING METHOTREXATE DERIVATIVE

[75] Inventor: Masahiko Mihara, Shizuoka-ken, Japan

[73] Assignee: Chugai Seiyaku Kabushiki Kaisha, Tokyo, Japan

[21] Appl. No.: 08/913,967

[22] PCT Filed: Mar. 26, 1996

[86] PCT No.: PCT/JP96/00780

§ 371 Date: Sep. 25, 1997

§ 102(e) Date: Sep. 25, 1997

[87] PCT Pub. No.: WO96/30019

PCT Pub. Date: Oct. 3, 1996

[30] Foreign Application Priority Data

Mar. 27, 1995 [JP] Japan .................................. 7-106817

[51] Int. Cl.$^6$ .................................................. A61K 31/505
[52] U.S. Cl. ............................................................ 514/258
[58] Field of Search ............................................... 514/258

[56] References Cited

U.S. PATENT DOCUMENTS

| | | | |
|---|---|---|---|
| 5,354,753 | 10/1994 | Ohi et al. ................................. | 514/258 |
| 5,728,692 | 3/1998 | Ohi et al. ............................. | 514/224.2 |

OTHER PUBLICATIONS

Mihara, M. et al., "Effect of Methotrexate Treatment on the Onset of Autoimmune Kidney Disease in Lupus Mice," *Chem. Pharm. Bull.,* 40–8:2177–2181 (1992).

Segal, R. et al., "Methotrexate Treatment in Murine Experimental Systemic Lupus Erythematosus (SLE); Clinical Benefits Associated with Cytokine Manipulation," *Clin. Exp. Immunol.,* 101:66–72 (1995).

Rothenberg, R. J. et al., "The Use of Methotrexate in Steriod–Resistant Systemic Lupus Erythematosus," *Arthritis and Rheumatism,* 31–5:612–615 (1988).

LeBlanc, B. A. E. W., et al., "Methotrexate in Systemic Lupus Erythmatosus," *The Journal of Rheumatology,* 21:836–838 (1994).

Wilson, K., et al., "A 2 Year, Open End Trail of Methotrexate in Systemic Lupus Erythematosus," *The Journal of Rheumatology,* 21:1674–1677 (1994).

Baggott, J. E. "Long–term Treatment of the MRL/lpr Mouse With Methotrexate and 10–Deazaaminofterin," *Agents Actions,* 35:104–111 (1992).

*Primary Examiner*—Raymond Henly, III
*Attorney, Agent, or Firm*—Browdy and Neimark

[57] ABSTRACT

Compounds represented by the general formula:

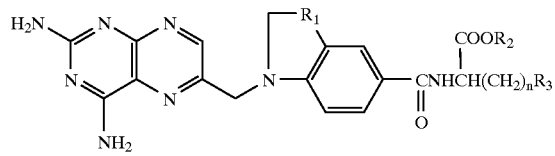

(where $R_1$ is one member selected from the group consisting of $CH_2$, $CH_2CH_2$, $CH_2O$, $CH_2S$ and $CH_2SO$; $R_2$ is a hydrogen atom or a lower alkyl group having 1–4 carbon atoms or a benzyl group; $R_3$ is a group represented by the general formula $COOR_4$, the general formula $NHCOR_5$, the general formula $CONR_6R_7$, $PO_3H_2$ or $SO_3H$; and n is an integer of 1–4) or salts therof are useful as therapeutic agents of autoimmune diseases such as systemic lupus erythematosus and nephritic diseases such as glomerulonephritis.

6 Claims, 5 Drawing Sheets

PHARMACEUTICAL AGENTS CONTAINING METHOTREXATE DERIVATIVE

This application is a 371 of PCT/JP96/00780 filed Mar. 26, 1996.

TECHNICAL FIELD

This invention relates to pharmaceutical agents containing methotrexate derivatives. More specifically, the invention relates to pharmaceutical agents containing methotrexate derivatives effective against autoimmune diseases (e.g. systemic lupus erythematosus) and glomerulonephritis.

BACKGROUND ART

Methotrexate (MTX) is an antifolate and is used for the treatment of acute leukemia, malignant lymphoma and other diseases. It is also known as an immunosuppressive drug and is primarily used for preventing acute graft-versus-host reactions in bone marrow transplantation. Furthermore, administration of low doses of MTX is known to be effective for the treatment of rheumatoid arthritis.

However, MTX causes comparatively severe side effects such as hepatotoxicity and fibrosis in lungs, which are often problematic in its clinical use. Consequently, development of drugs are desired that have strong efficacy and minimal side effects.

DISCLOSURE OF INVENTION

An object of the invention is to provide therapeutic agents for autoimmune diseases (e.g. systemic lupus erythematosus) and glomerulonephritis that are excellent in terms of balance of efficacy and side effects.

As a result of intensive studies conducted to attain the above-stated object, the present inventors found that compounds represented by the general formula (I):

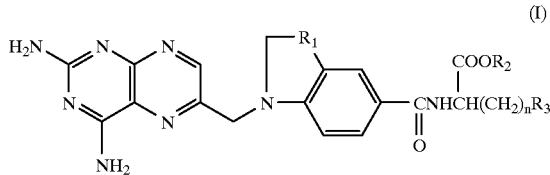

atoms or an optionally substituted phenyl group or a carboxyalkyl group or a lower alkylsulfonyl group) or a group represented by $PO_3H_2$ or $SO_3H$; n is an integer of 1–4, or salts thereof are useful as therapeutic agents for autoimmune diseases (e.g. systemic lupus erythematosus) and glomerulonephritis. The present invention has been accomplished on the basis of this finding.

Thus, the present invention relates to a therapeutic agent for autoimmune diseases (e.g. systemic lupus erythematosus) and glomerulonephritis which contains a compound represented by the general formula (I):

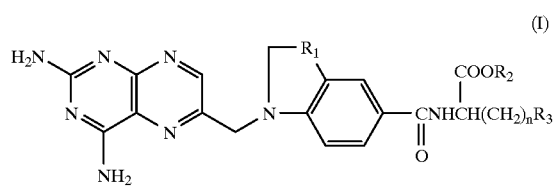

where $R_1$ is one member of the group consisting of $CH_2$, $CH_2CH_2$, $CH_2O$, $CH_2S$ and $CH_2SO$; $R_2$ is a hydrogen atom or a lower alkyl group having 1–4 carbon atoms or a benzyl group; $R_3$ is a group represented by the general formula $COOR_4$ (where $R_4$ is a hydrogen atom or a lower alkyl group having 1–4 carbon atoms) or the general formula $NHCOR_5$ (where $R_5$ is an optionally substituted phenyl group) or the general formula $CONR_6R_7$ (where $R_6$ is a hydrogen atom or a lower alkyl group having 1–4 carbon atoms, and $R_7$ is a lower alkyl group having 1–4 carbon atoms or an optionally substituted phenyl group or a carboxyalkyl group or a lower alkylsulfonyl group) or a group represented by $PO_3H_2$ or $SO_3H$; n is an integer of 1–4, or a salt thereof as an active ingredient.

The invention also relates to a therapeutic agent for autoimmune diseases (e.g. systemic lupus erythematosus) and glomerulonephritis which contains a compound represented by the general formula (II):

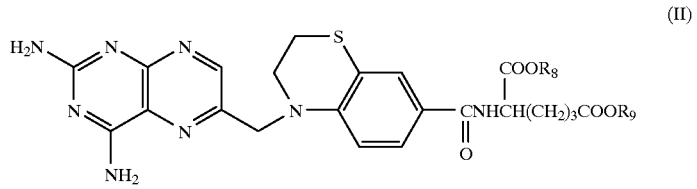

where $R_1$ is one member selected from the group consisting of $CH_2$, $CH_2CH_2$, $CH_2O$, $CH_2S$ and $CH_2SO$; $R_2$ is a hydrogen atom or a lower alkyl group having 1–4 carbon atoms or a benzyl group; $R_3$ is a group represented by the general formula $COOR_4$ (where $R_4$ is a hydrogen atom or a lower alkyl group having 1–4 carbon atoms) or the general formula $NHCOR_5$ (where $R_5$ is an optionally substituted phenyl group) or the general formula $CONR_6R_7$ (where $R_6$ is a hydrogen atom or a lower alkyl group having 1–4 carbon atoms, and $R_7$ is a lower alkyl group having 1–4 carbon where $R_8$ and $R_9$ which may be the same or different represent a hydrogen atom or a lower alkyl group having 1–4 carbon atoms, or a salt thereof as an active ingredient.

The compounds of the invention which are represented by the general formula (I) are described in International Publication WO 92/03436, which discloses data showing the ability of the compounds to suppress the proliferation of human lymphocytes, rat and human keratinocytes and mouse cancer cells (P388, colon 26) and suggests the utility of the compounds as therapeutic agents for rheumatoid arthritis, psoriasis and cancers on the basis of the experimental results. In addition, International Publication WO 94/14810 discloses data showing that compounds represented by the general formula (II) have an inhibitory effect on the proliferation of synovial cells derived from rheumatoid arthritis patients, thus suggesting the utility of the compounds as antirheumatics.

However, no report has yet been made showing that compounds represented by the general formula (I) are effective against diseases such as systemic lupus erythematosus and glomerulonephritis.

BEST EMBODIMENT FOR CARRYING OUT THE INVENTION

Figure 1:
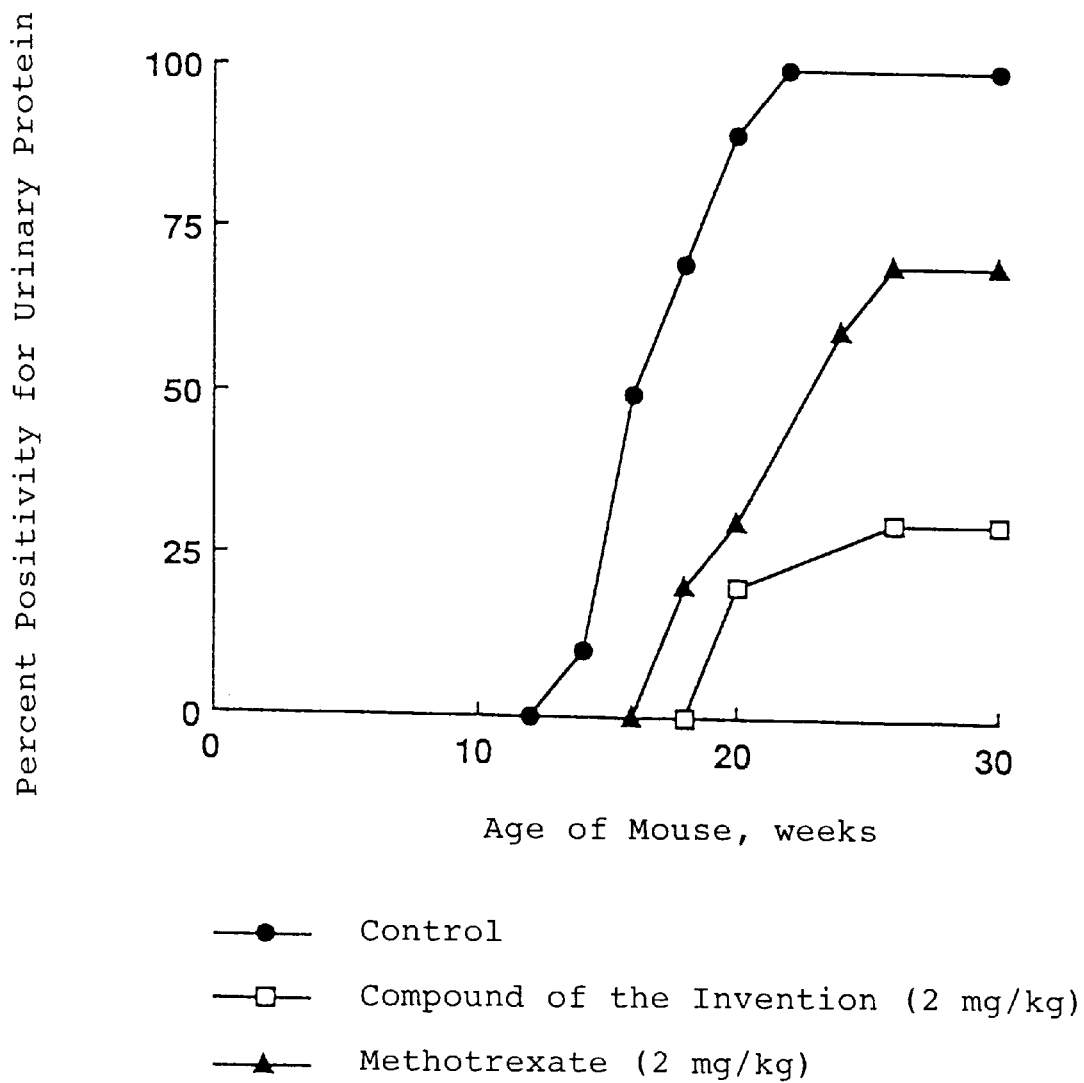
FIG. 1 is a graph showing the suppressive effect of various drugs on urinary protein excretion from MRL/lpr mice.

The pharmaceutical agents of the invention are useful in the treatment of autoimmune diseases such as systemic lupus erythematosus and autoimmune glomerulonephritis. The agents are particularly useful in the treatment of lupus nephritis. The pharmaceutical agents of the invention are also useful in the treatment of nephritis, in particular, glomerulonephritis. Examples of glomerulonephritis include not only lupus nephritis but also nephritis caused by polyarteritis nodosa, nephritis caused by Schönlein-Henoch purpura, nephritis caused by Weigner's granulomatosis and Goodpasture's syndrome.

The "lower alkyl group" as used in the invention refers to straight- or branch-chained alkyl groups having 1–6 carbon atoms unless otherwise specified by carbon number, and preferred examples include methyl, ethyl, n-propyl, isopropyl, n-butyl, isobutyl, sec-butyl, tert-butyl groups, etc.

The "substituent" refers to lower alkyl, hydroxyl, amino, halogeno, cyano, lower alkyloxy, mercapto, acyl, acyloxy, phenyl, carboxyl, lower alkyloxycarbonyl groups, etc., and preferred examples include carboxyl, lower alkyloxycarbonyl groups, etc.

The "carboxyalkyl group" refers to lower alkyl group substituted by one or more carboxyl groups and preferred examples include lower alkyl groups substituted by one carboxyl group, more preferred examples including a 3-carboxypropyl group.

Preferred examples of the lower alkylsulfonyl group include a methanesulfonyl group, etc.

The compounds of the invention may be used in the form of salts obtainable by conventional methods. Usable salts include: inorganic acid salts such as hydrochlorides, hydrobromides, hydroiodies, sulfates and phosphates; organic acid salts such as succinates, malonates, acetates, maleates, fumarates, citrates, gluconates, mandelates, benzoates, salicylates, methanesulfonates, benzenesulfonates and p-toluenesulfonates; and metal salts such as sodium, potassium and magnesium salts; inorganic and organic acid salts are preferred, with hydrobromides and methanesulfonates being particularly preferred.

Compounds preferred for use as therapeutic agents of the invention are those described in the Examples of International Publications WO 92/03436 and WO 94/14810 and the most preferred compounds are those described in the Examples of International Publication WO 94/14810.

Pharmaceutical agents containing the compounds of the invention can be administered either perorally or parenterally, with peroral administration being particularly preferred. The dose varies with the type of the disease to be treated, the body weight of the patient, symptoms and the like, and the usual dose ranges from 0.01 to 100 mg/day/person.

The pharmaceutical agents containing the compounds of the invention can take various dosage forms including solutions (e.g. injections), tablets, capsules and powders.

EXAMPLES

The following examples are provided to further illustrate the present invention. In the examples, N-(1-((2,4-diamino-6-pteridinyl)methyl)-3,4-dihydro-2H-1,4-benzothiazine-7-carbonyl)-L-α-aminoadipic acid of the following formula.

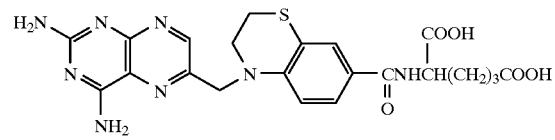

was used as the drug of the invention. Methotrexate was used as a control drug.

Example 1

Test of Administration to MRL/lpr Mouse

Figure 2:
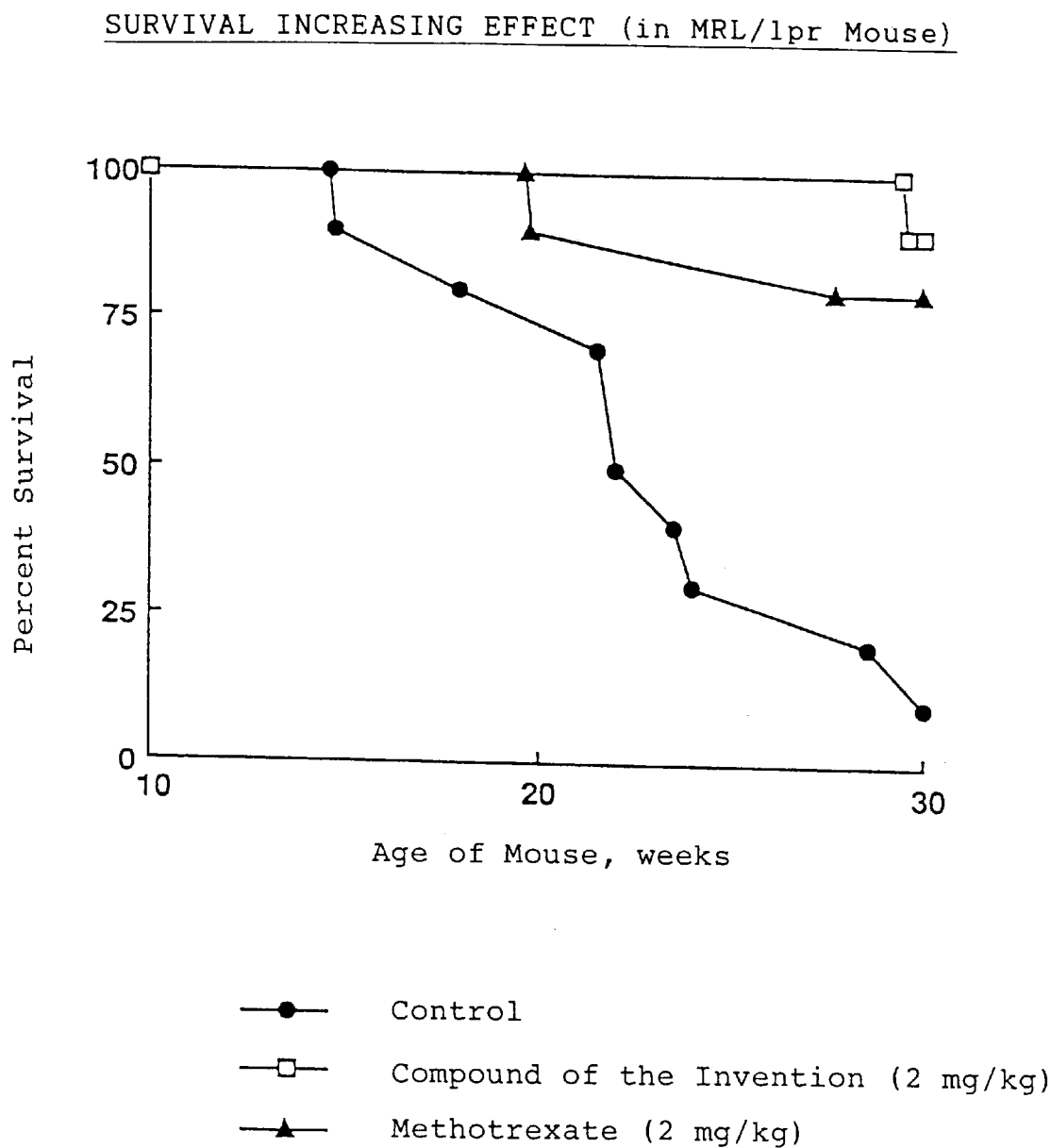
FIG. 2 is a graph showing the prolongation of the survival of MRL/lpr mice by various drugs.

Eight-week old female MRL/lpr mice (10 animals per group) were orally administered with each drug (2 mg/kg) and PBS (control) three times a week until they were 30-week old, and excretion of urinary protein was measured with COMBISTICKS paper (Miles-Sankyo). The individuals showing a urinary protein over 100 mg/dL were evaluated as "positive". The results are shown in FIG. 1. The days of survival of each mouse were also checked. The results are shown in FIG. 2.

In the control group, excretion of urinary protein occurred in the 12-week old mice and all cases that were 22-week old were positive. In contrast, the group of animals administered with the compound of the invention showed a significant delay in the appearance of urinary protein and onset of the disease was suppressed until after the animals were 30-week old. The suppressive effect was also observed in the MTX administered group, but the effect of MTX was obviously weaker than the compound of the invention. In terms of the survival, the group of animals administered with the compound of the invention showed an obvious prolongation and there was only one case of death before the animals were 30-week old. This effect may well be considered to be stronger than that of MTX.

Example 2

Test of Administration to NZB/WF1 Mouse

Figure 3:
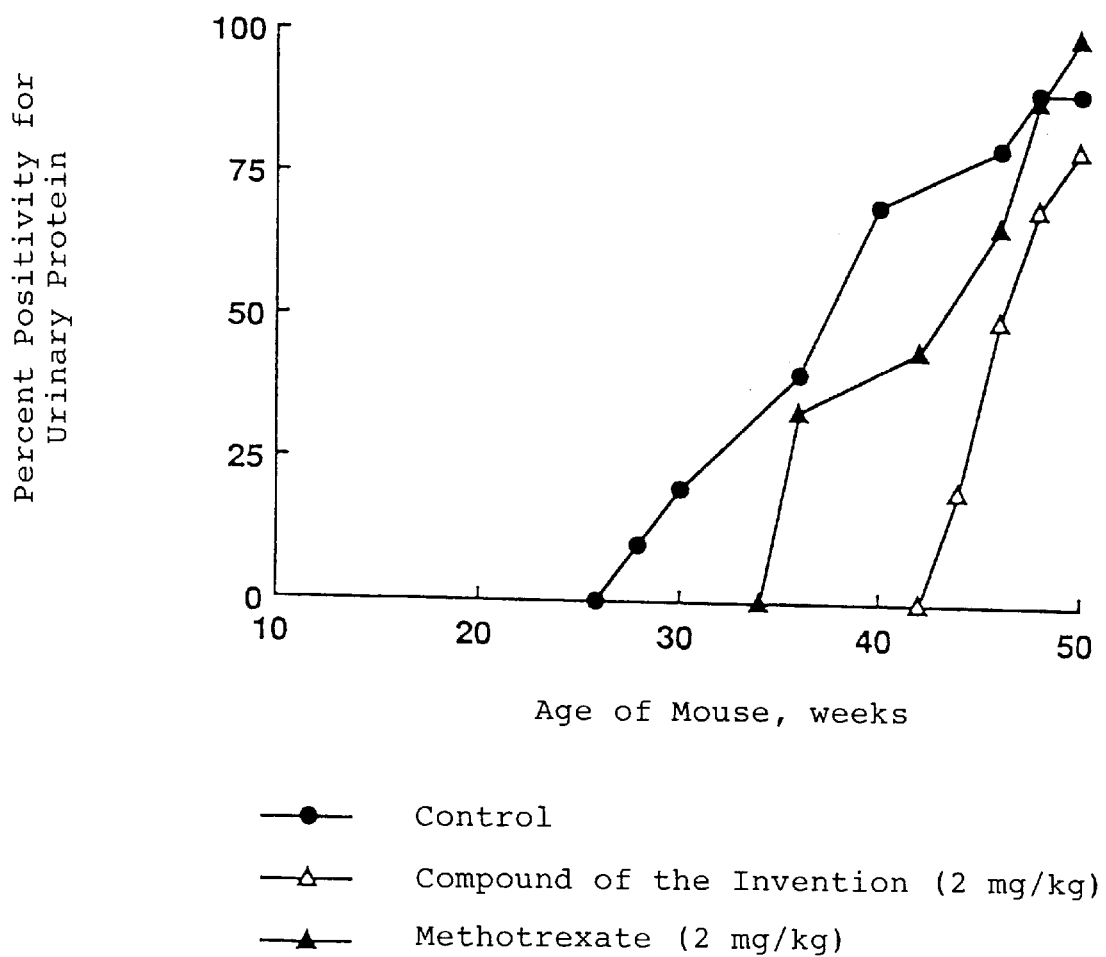
FIG. 3 is a graph showing the suppressive effect of various drugs on urinary protein excretion from NZB/WF1 mice.
Figure 4:
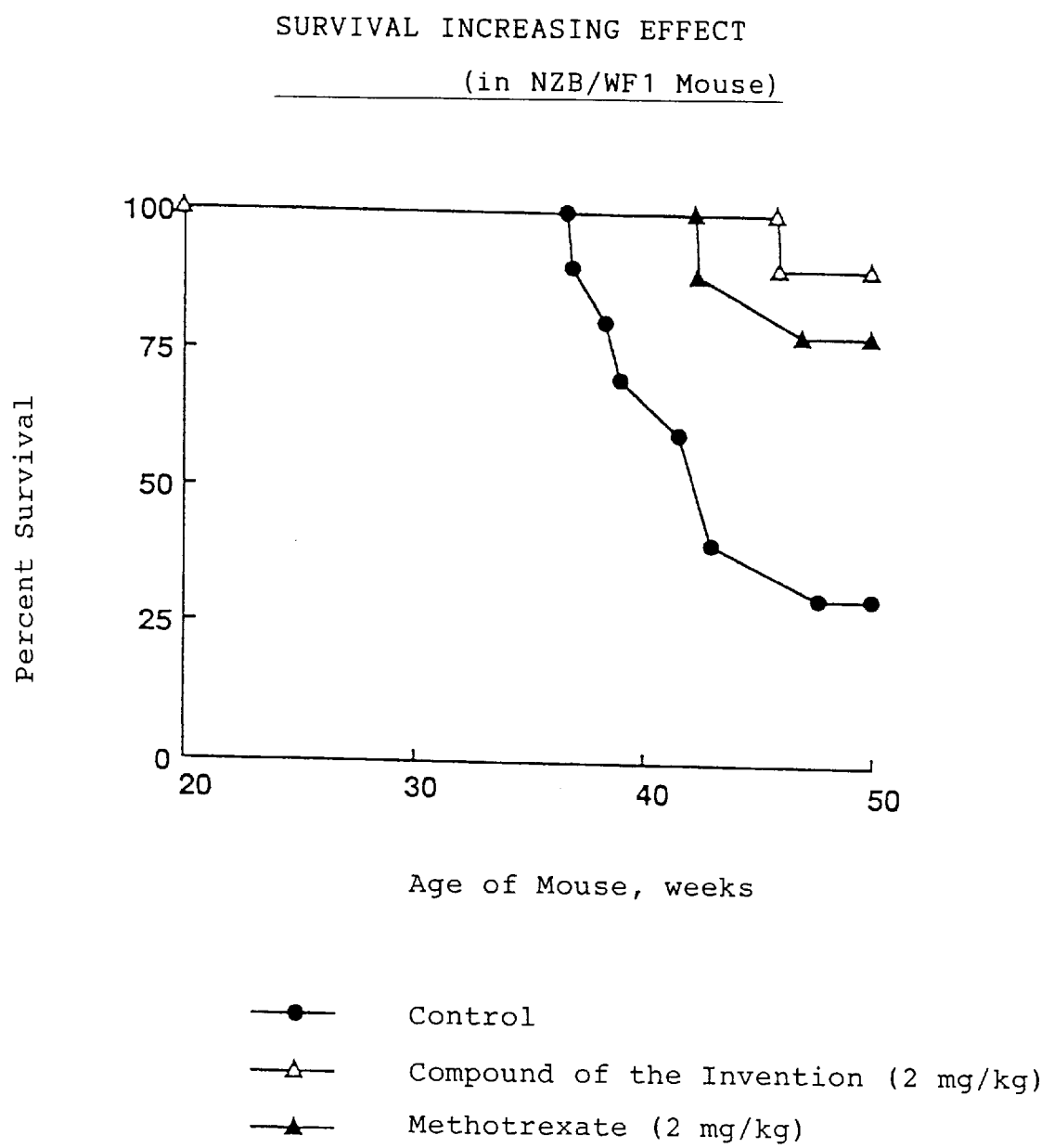
FIG. 4 is a graph showing the prolongation of the survival of NZB/WF1 mice by various drugs.
Figure 5:
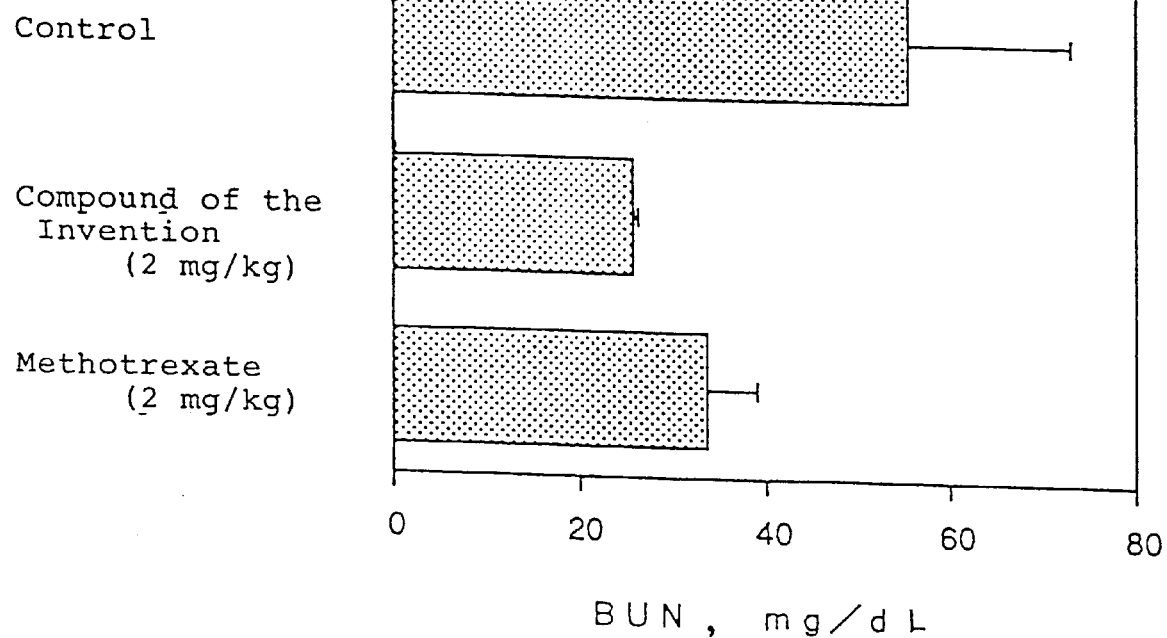
FIG. 5 is a graph showing the suppressive effect of various drugs on the elevation of BUN in NZB/WF1 mice.

Twelve-week old female NZB/WF1 mice (10 animals per group, except for the MTX administered group consisting of 9 animals per group) were orally administered with each drug (2 mg/kg) and control (PBS) three times a week until they were 40-week old, and their excretion of urinary protein and BUN were measured. The measurement of urinary protein excretion was done by COMBISTICKS paper (Miles-Sankyo) and the individuals showing a urinary protein over 100 mg/dL were evaluated as "positive". The results are shown in FIG. 3. The survival time of each mouse were also checked. The results are shown in FIG. 4. BUN measurements were conducted on the 40-week old animals using UNIKIT-BUNs by means of a rapid blood analyzer. The results (mean±standard error) are shown in FIG. 5.

As in Example 1, the compound of the invention was found to have stronger effects than MTX on the suppression of urinary protein excretion and the prolongation of survival time. It was also found to be capable of suppressing the elevation of BUN due to the onset of glomerulonephritis.

Thus, the suppression of proteinuria excretion and the prolongation of survival, etc. were observed when the compound of the invention was administered to MRL/lpr and NZB/WF1 mice which were known as model animals for systemic lupus erythematosus and glomerulonephritis. This fact shows that the compounds of the invention are useful as therapeutic agents of nephritic diseases such as glomerulonephritis and autoimmune diseases, in particular, systemic lupus erythematosus.

INDUSTRIAL APPLICABILITY

The above results demonstrates that the pharmaceutical agents of the invention which contain methotrexate derivatives are useful as therapeutic agents of nephritic diseases such as glomerulonephritis and auto-immune diseases such as systemic lupus erythematosus.

I claim:

1. A method for the treatment of an autoimmune disease selected from the group consisting of systemic lupus erythematosus, autoimmune nephritis and glomerulonephritis, in a patient in need of said treatment, comprising
administering to said patient an amount effective for said treatment of a composition comprising as active ingredient a compound of formula (I):

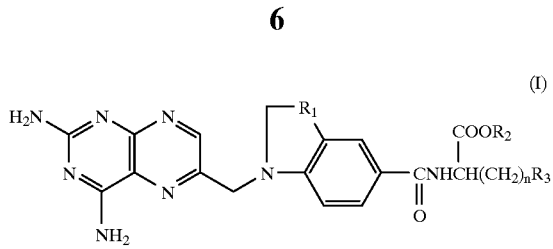

where $R_1$ is selected from the group consisting of $CH_2$, $CH_2CH_2$, $CH_2O$, $CH_2S$ and $CH_2SO$;

$R_2$ is a hydrogen atom or a lower alkyl group having 1–4 carbon atoms or a benzyl group;

$R_3$ is a group represented by the formula $COOR_4$, where $R_4$ is a hydrogen atom or a lower alkyl group having 1–4 carbon atoms, or the formula $NHCOR_5$, where R5 is an optionally substituted phenyl group, or the formula $CONR_6R_7$, where $R_6$ is a hydrogen atom or a lower alkyl group having 1–4 carbon atoms, and $R_7$ is a lower alkyl group having 1–4 carbon atoms or an optionally substituted phenyl group or a carboxyalkyl group or a lower alkylsulfonyl group, or a group represented by $PO_3H_2$ or $SO_3H$; n is an integer of 1–4, or a salt thereof, and a pharmaceutical excipient.

2. The method of claim 1 wherein said patient is one whose autoimmune disease is systemic lupus erythematosus.

3. The method of claim 1 wherein said patient is one whose autoimmune disease is autoimmune nephritis.

4. The method of claim 1 wherein said patient is one whose autoimmune disease is glomerulonephritis.

5. The method of claim 1 wherein said patient is one whose autoimmune disease is lupus nephritis.

6. A method for the treatment of an autoimmune disease selected from the group consisting of systemic lupus erythematosus, autoimmune nephritis and glomerulonephritis, in a patient in need of said treatment, comprising
administering to said patient an amount effective for said treatment of a compound of formula (II):

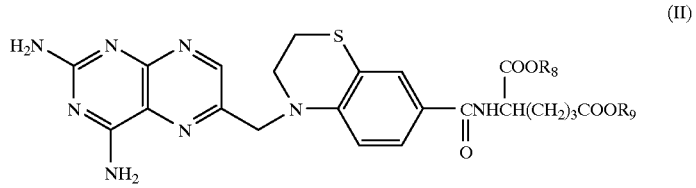

where $R_8$ and $R_9$ which may be the same or different represent a hydrogen atom or a lower alkyl group having 1–4 carbon atoms, or a salt thereof.

* * * * *